United States Patent
Buchanan et al.

(10) Patent No.: US 9,029,621 B2
(45) Date of Patent: May 12, 2015

(54) SELECTIVE OLIGOMERIZATION OF ISOBUTENE

(75) Inventors: John Scott Buchanan, Lambertville, NJ (US); Jane Chi-Ya Cheng, Bridgewater, NJ (US); Jihad Mohammed Dakka, Whitehouse Station, NJ (US); Jon Edmond Stanat, Westhampton Beach, NY (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 1385 days.

(21) Appl. No.: 12/674,443

(22) PCT Filed: Oct. 2, 2008

(86) PCT No.: PCT/US2008/078585
§ 371 (c)(1),
(2), (4) Date: Jul. 27, 2011

(87) PCT Pub. No.: WO2009/055227
PCT Pub. Date: Apr. 30, 2009

(65) Prior Publication Data
US 2011/0282120 A1    Nov. 17, 2011

Related U.S. Application Data

(60) Provisional application No. 60/982,984, filed on Oct. 26, 2007.

(30) Foreign Application Priority Data

Mar. 4, 2008    (EP) ................... 08003993

(51) Int. Cl.
| C07C 2/12 | (2006.01) |
| C07C 2/66 | (2006.01) |
| C07C 7/177 | (2006.01) |
| C07C 15/02 | (2006.01) |
| C07C 37/08 | (2006.01) |
| C07C 39/04 | (2006.01) |
| C07C 41/05 | (2006.01) |
| C07C 45/53 | (2006.01) |

(52) U.S. Cl.
CPC ... *C07C 2/12* (2013.01); *C07C 2/66* (2013.01); *C07C 7/177* (2013.01); *C07C 15/02* (2013.01); *C07C 37/08* (2013.01); *C07C 39/04* (2013.01); *C07C 41/05* (2013.01); *C07C 45/53* (2013.01); *C07C 2529/70* (2013.01)

(58) Field of Classification Search
CPC ............. C07C 7/177; C07C 2529/70
USPC ......... 585/502, 510, 520, 530, 532, 533, 312, 585/319, 323, 446, 448, 467
See application file for complete search history.

(56) References Cited

U.S. PATENT DOCUMENTS

| 2,276,199 | A | 3/1942 | Kassel |
| 2,282,469 | A | 5/1942 | Frolich |
| 2,584,103 | A | 2/1952 | Pines et al. |
| 3,325,465 | A | 6/1967 | Jones et al. |
| 3,819,735 | A | 6/1974 | Argento et al. |
| 4,051,191 | A | 9/1977 | Ward |
| 4,058,576 | A | 11/1977 | Chang et al. |
| 4,144,138 | A | 3/1979 | Rao et al. |
| 4,377,393 | A * | 3/1983 | Schleppinghoff .............. 44/449 |
| 4,454,367 | A | 6/1984 | Sakurada et al. |
| 4,471,154 | A | 9/1984 | Franklin |
| 4,490,565 | A | 12/1984 | Chang et al. |
| 4,490,566 | A | 12/1984 | Chang et al. |
| 4,822,921 | A | 4/1989 | Knifton et al. |
| 4,891,458 | A | 1/1990 | Innes et al. |
| 4,956,514 | A | 9/1990 | Chu |
| 4,992,606 | A | 2/1991 | Kushnerick et al. |
| 5,059,736 | A | 10/1991 | Tamura et al. |
| 5,065,794 | A | 11/1991 | Cheung |
| 5,081,323 | A | 1/1992 | Innes et al. |
| 5,091,590 | A | 2/1992 | Harandi et al. |
| 5,177,283 | A | 1/1993 | Ward |
| 5,183,945 | A | 2/1993 | Stibrany et al. |

(Continued)

FOREIGN PATENT DOCUMENTS

| DE | 2 300 903 | 8/1973 |
| DE | 35 42171 | 6/1987 |

(Continued)

OTHER PUBLICATIONS

Isakov et al., "*Catalytic Properties of Palladium-Zeolite Systems in the Synthesis of Sec-Butylbenzene From Benzene and Ethylene*", Inst. Org. Khim, im. N. D. Zelinskogo, Moscow, Russia, Neftekhimiya, 1994, vol. 34, No. 2, pp. 151-170 (Abstract Only; XP002317126).

Isakov et al., "*Study of Polyfunctional Zeolite Catalysts. Communication 2. Formation of a Catalyst for Synthesis Off Sec-Butylbenzene Prepared From Nickel Acetylacetonate and Cay Zeolite*", Inst. Org. Khim. im. Zelinskogo, Moscow, USSR, Izv. Akad Nauk SSSR, Ser. Khim., 1976, vol. 3, pp. 498-504 (Abstract Only).

Minachev et al., "*Study of the Nature of Bifunctional Catalysts for the Synthesis of Sec-Butylbenzene From Ethylene and Benzene*", Inst. Org. Khim, im. Zelinskogo, Moscow, USSR, Geterog. Katal., 1979, Pt. 2, pp. 485-492 (Abstract Only).

(Continued)

Primary Examiner — Thuan D Dang

(57) ABSTRACT

A process for oligomerizing isobutene comprises contacting a feedstock comprising isobutene with a catalyst comprising a MCM-22 family molecular sieve under conditions effective to oligomerize the isobutene, wherein said conditions including a temperature from about 45° C. to less than 140° C. The isobutene may be a component of a hydrocarbon feedstock containing at least one additional $C_4$ alkene. In certain aspects, isobutene oligomers are separated from a first effluent of the oligomerization to produce a second effluent comprising at least one n-butene. The second effluent can be contacted with an alkylation catalyst to produce sec-butylbenzene.

17 Claims, 2 Drawing Sheets

(56) References Cited

U.S. PATENT DOCUMENTS

| | | | |
|---|---|---|---|
| 5,264,643 A * | 11/1993 | DiGuiseppi et al. | 585/533 |
| 5,298,667 A | 3/1994 | Iwanaga et al. | |
| 5,336,820 A | 8/1994 | Owen et al. | |
| 5,368,691 A | 11/1994 | Asselineau et al. | |
| 5,371,310 A | 12/1994 | Bennett et al. | |
| 5,387,721 A | 2/1995 | Kruse et al. | |
| 5,401,429 A | 3/1995 | Flynn et al. | |
| 5,557,024 A | 9/1996 | Cheng et al. | |
| 5,723,710 A | 3/1998 | Gajda et al. | |
| 5,910,528 A | 6/1999 | Falicoff et al. | |
| 5,922,920 A | 7/1999 | Bond et al. | |
| 6,002,057 A | 12/1999 | Hendriksen et al. | |
| 6,051,521 A | 4/2000 | Cheng et al. | |
| 6,169,215 B1 | 1/2001 | Levin et al. | |
| 6,169,216 B1 | 1/2001 | Levin et al. | |
| 6,274,783 B1 | 8/2001 | Gildert et al. | |
| 6,275,783 B1 | 8/2001 | Okamura | |
| 6,297,406 B1 | 10/2001 | Levin et al. | |
| 6,410,804 B1 | 6/2002 | Levin et al. | |
| 6,440,886 B1 | 8/2002 | Gajda et al. | |
| 6,500,999 B2 * | 12/2002 | Di Girolamo et al. | 585/510 |
| 6,657,090 B2 | 12/2003 | Rix et al. | |
| 6,720,462 B2 | 4/2004 | Kuhnle et al. | |
| 6,914,166 B2 | 7/2005 | Dakka et al. | |
| 7,112,711 B2 | 9/2006 | Mathys et al. | |
| 2002/0078622 A1 | 6/2002 | Rix et al. | |
| 2002/0183576 A1 * | 12/2002 | Flego et al. | 585/533 |
| 2003/0083527 A1 | 5/2003 | Kuhnle et al. | |
| 2007/0213576 A1 | 9/2007 | Brown et al. | |
| 2008/0086018 A1 | 4/2008 | Cheng et al. | |

FOREIGN PATENT DOCUMENTS

| | | | |
|---|---|---|---|
| EP | 0 390 596 | 10/1990 | |
| EP | 0 736 584 | 10/1996 | |
| EP | 0 994 088 | 4/2000 | |
| EP | 1 088 809 | 4/2001 | |
| GB | 797986 | 7/1958 | |
| JP | 2002-282698 | 10/2002 | |
| SU | 417405 | 8/1974 | |
| SU | 265349 | 10/1976 | |
| SU | 1245564 | 7/1986 | |
| WO | 91/18851 | 12/1991 | |
| WO | WO 2006/015826 A * | 2/2006 | C07C 2/70 |
| WO | 2007/094938 | 8/2007 | |

OTHER PUBLICATIONS

Minachev et al., "*Alkylation of Benzene by Ethylene on Catalysts Produced From Synthetic Zeolites Ultrasil*", Inst. Org. Khim, im. Zelinskogo, Moscow, USSR, Neftekhimiya, 1988, vol. 28, No. 2, pp. 151-158 (Abstract Only: XP-002317128).

Minachev et al., "*Bifunctional Catalysts for the Alkylation of Aromatic Compounds by Ethylene*", USSR, Lektsii-Vses, Shk. Katal, 1981, vol. 2, pp. 76-111 (Abstract Only: XP-002317129).

Ohkubo et al., "*A Kinetic Study on the Homogeneous Liquid-Phase Oxidation of Cumene in the Presence of Triphenylsulfonium Chloride*", Bull. Chem. Soc., Japan, 1969, vol. 42, No. 7, pp. 1800-180.

Sachanen et al., "*High-Temperature Alkylation of Aromatic Hydrocarbons*", Ind. Eng. Chem., vol. 33, No. 12, 1941, pp. 1540-1544.

Yen, "*Phenol*", Process Economics Report No. 22B, Stanford Research Institute, Dec. 1977, pp. 113-124, 261 and 263.

Hauge K, et al. "*Oligomerization of isobutene over solid acid catalysts*", Catalysis Today, 2005, vol. 100, pp. 463-466.

Marchionna M., et al. "*Light olefins dimerization to high quality gasoline components*", Catalysis Today, 2001, vol. 65 pp. 397-403.

\* cited by examiner

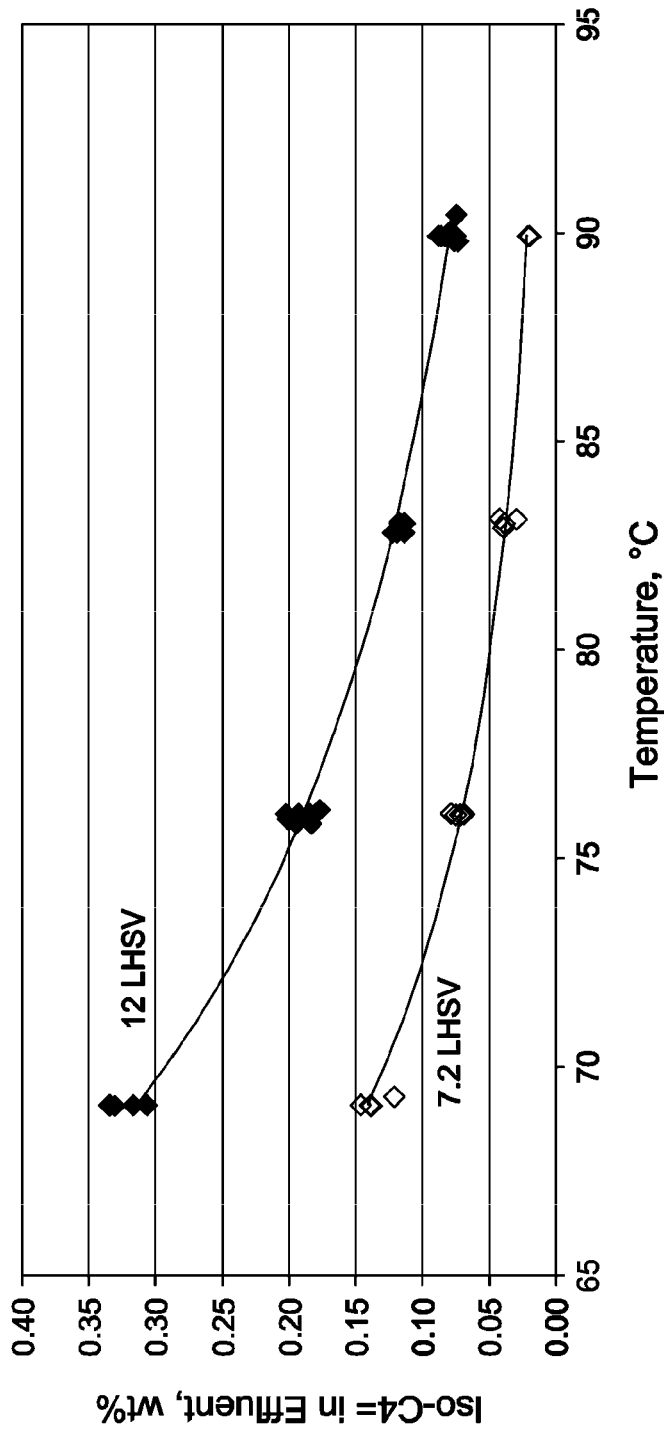

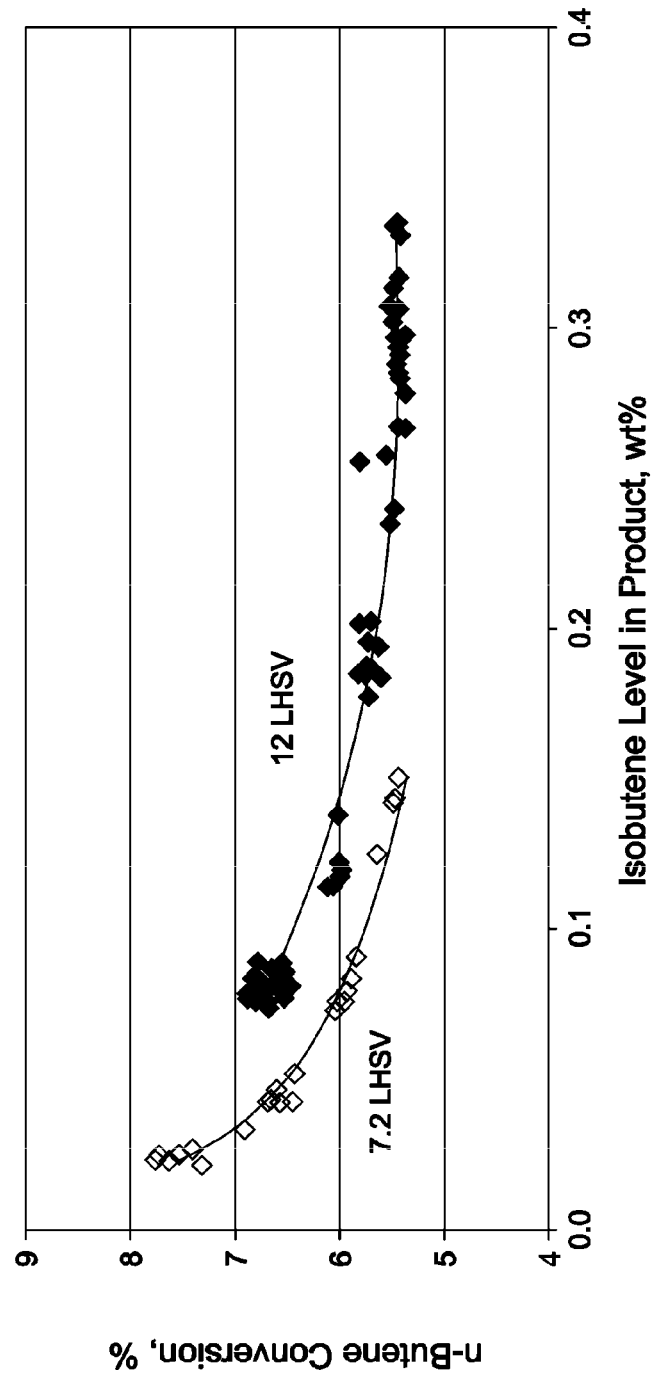

US 9,029,621 B2

SELECTIVE OLIGOMERIZATION OF ISOBUTENE

CROSS-REFERENCE TO RELATED APPLICATIONS

This application is a National Stage Application of International Application No. PCT/US2008/078585 filed Oct. 2, 2008, which claims priority from U.S. Ser. No. 60/982,984 filed Oct. 26, 2007, both of which are incorporated herein by reference.

FIELD

The present invention relates to the selective oligomerization of isobutene.

BACKGROUND

The selective oligomerization of isobutene is an important chemical reaction, particularly where the isobutene is contained in a refinery $C_4$ hydrocarbon stream, such as Raffinate-1 and Raffinate-2.

For example, $C_4$ linear olefins are an attractive feedstock for producing octenes with zeolite catalysts because, among other reasons, the resulting octenes have triple branching of less than about 5 wt %. However, when isobutene is present in significant quantities (>10 wt %) in the oligomerization feedstock, such as with Raffinate-1, the amount of triple-branched octenes increases to a level which is unacceptable for some end uses such as certain plasticizers. In the past, this problem was generally addressed by selectively reacting the isobutene with methanol to produce methyl t-butyl ether (MTBE). However, with the phase-out of MTBE because of environmental concerns, this reaction is no longer an attractive method of removing isobutene. As a result, interest has focused on selective dimerization of the isobutene to produce octenes useful as, for example, gasoline octane enhancers and as feedstocks for producing $C_9$ aldehydes and/or alcohols.

Another use for the selective oligomerization of isobutene is in the purification of $C_4$ olefin streams used in the alkylation of benzene to produce sec-butylbenzene, an important precursor in the production of phenol. Thus, even when present at only low levels (<5 wt %) in a $C_4$ olefin stream, such as Raffinate-2, isobutene reacts with benzene to produce tert-butylbenzene. However, tert-butylbenzene is difficult to separate from sec-butylbenzene by distillation since the boiling points of the two butylbenzene isomers are very similar, 169° C. for tert-butylbenzene as compared with 173° C. for sec-butylbenzene. Moreover, tert-butylbenzene is known to be an inhibitor to the oxidation of sec-butylbenzene to the corresponding hydroperoxide, which is the first step in the conversion of sec-butylbenzene to phenol and methyl ethyl ketone.

One example of a process for the dimerization of isobutene is disclosed in U.S. Pat. No. 6,914,166, in which a $C_4$ olefinic feedstock containing isobutene and n-butene(s) is contacted with dealuminated zeolite beta under conditions including a temperature below 50° C. effective to allow selective dimerization of isobutene to trimethylpentene(s). However, although this process appears to be highly selective for isobutene conversion, the catalyst is found to age rapidly at the conditions employed.

U.S. Pat. No. 6,274,783 discloses a process for the concurrent dimerization and hydrogenation of isobutene in a single distillation column reactor containing both a dimerization catalyst, such as a zeolite or an acidic cation exchange resin, and a hydrogenation catalyst, such as a Group VIII metal deposited on a carrier or support. There is no indication that the process would selectively dimerize isobutene in a mixed $C_4$ olefin feed.

U.S. Pat. No. 6,500,999 discloses a process for the production of hydrocarbons with a high octane number starting from hydrocarbon cuts containing isobutene by means of selective dimerization with acid catalysts, wherein the dimerization reaction is carried out in a tubular reactor using a feed containing isobutene in quantities of less than 20% by weight and with a molar ratio of linear olefins/isobutene greater than 3, preferably operating at a reaction temperature ranging from 30 to 120° C., at a pressure of less than 5 MPa and at feed space velocities of less than 60 hr$^{-1}$. Suitable acid catalysts are said to include phosphoric acid supported on a solid carrier, a cationic acid exchange resin, a liquid acid, a sulfonic acid derivative, a silico-alumina, a mixed oxide, a zeolite or a fluorinated or chlorinated alumina.

U.S. Pat. No. 7,112,711 discloses a process for oligomerizing alkenes having from 3 to 6 carbon atoms, including isobutene, in the presence of a catalyst containing a zeolite of the MFS structure type. The process is carried out at a temperature comprised between 125 and 175° C. when the feedstock contains only alkenes with 3 carbon atoms and between 140 and 240° C. when the feedstock contains at least one alkene with 4 or more carbon atoms U.S. Patent Application Publication No. 2007/0213576, published Sep. 13, 2007, discloses a process for the dimerization of isobutene at a temperature in excess of 240° C. in the presence of a multi-dimensional molecular sieve catalyst containing at least one 10 or 12 ring channel, such as ZSM-57, ZSM-5, FAU, Beta, ZSM-12, mordenite, MCM-22 family zeolites, and mixtures thereof to produce a product low in triple-branched octenes.

K. Hauge et al in *Catalysis Today*, Vol. 100 (2005) pp. 463-466 reported on the oligomerization of pure isobutene over solid acid catalysts at 40° C. and 10 bar pressure and 60 WHSV. The zeolite solid acid catalysts (ZSM-5, beta, and Y) had high initial activity, but the activity dropped drastically over the course of 2 hours. This was attributed to "the production of high molecular weight oligomers inside the zeolite pores." The macroreticular acidic resin Amberlyst 15, in contrast, showed activity that leveled out after about 2 hours.

According to the present invention, it has now been found that, when operated at low temperature, molecular sieves of the MCM-22 family are selective and stable catalysts for the oligomerization of isobutene in the presence of other $C_4$ alkenes. Although the reason for this result is not understood, it is believed that the presence of the active acid sites in pockets on the external surface of the zeolite crystal in MCM-22 molecular sieves allows the reaction products to quickly desorb, thereby avoiding the production of high molecular weight oligomers inside the zeolite pores as reported by K. Hauge et al in *Catalysis Today*, Vol. 100.

SUMMARY

In one aspect, the invention resides in a process for oligomerizing isobutene, the process comprising contacting a feedstock comprising isobutene with a catalyst comprising a MCM-22 family molecular sieve under conditions effective to oligomerize said isobutene, said conditions including a temperature from about 45° C. to less than 140° C.

Conveniently, said conditions include a temperature from about 50° C. to about 120° C. and/or a pressure of from about 345 to 1379 kPag (about 50 to about 2000 psig).

Conveniently, the molecular sieve has an X-ray diffraction pattern including d-spacing maxima at 12.4±0.25, 6.9±0.15, 3.57±0.07 and 3.42±0.07 Angstrom. Generally, the molecular sieve is selected from MCM-22, PSH-3, SSZ-25, ERB-1, ITQ-1, ITQ-2, MCM-36, MCM-49, MCM-56, UZM-8, and combinations of any two or more thereof, especially from MCM-22, MCM-49, MCM-56 and combinations of any two or more thereof.

In one embodiment, the feedstock also comprises at least one additional $C_4$ alkene, such as n-butene.

In a further aspect, the invention resides in a process for producing sec-butylbenzene, the process comprising:

(a) contacting a $C_4$ hydrocarbon feedstock comprising isobutene and at least one n-butene with a catalyst comprising a MCM-22 family molecular sieve under conditions effective to selectively oligomerize the isobutene, said conditions including a temperature from about 45° C. to less than 140° C. and said contacting producing an effluent comprising isobutene oligomers and said at least one n-butene;

(b) separating said at least one n-butene from the effluent;

(c) contacting said at least one n-butene separated in (b) with benzene under alkylation conditions and in the presence of an alkylation catalyst to produce sec-butylbenzene.

In one embodiment, said $C_4$ hydrocarbon feedstock comprises up to 5 wt % isobutene for example from 2 to 5 wt %, such as from 3 to 5 wt % isobutene. Preferably the conditions are selected such that the effluent contains less than 0.3 wt % isobutene, such as less than 0.2 wt % isobutene, for example from 0.01 to 0.2 wt % isobutene. In a further embodiment, said $C_4$ hydrocarbon feedstock comprises at least 90 wt % of n-butenes and the conditions and catalyst are selected such that said contacting (a) oligomerizes no more than 12 wt % of said n-butenes.

Conveniently, the process further comprises (d) contacting the effluent with water and/or an alcohol prior to said separating (b), said contacting (d) converting at least part of any isobutene remaining in the effluent to an ether.

In one embodiment, the alkylation catalyst comprises a MCM-22 family molecular sieve.

Conveniently, the process further comprises:

(e) oxidizing the sec-butylbenzene from (c) to produce a hydroperoxide; and (f) cleaving the hydroperoxide from (e) to produce phenol and methyl ethyl ketone.

BRIEF DESCRIPTION OF THE DRAWINGS

FIG. 1 is a graph of product isobutene concentration against temperature in the butene oligomerization process of Example 1.

FIG. 2 is a graph of n-butene conversion against product isobutene concentration in the butene oligomerization process of Example 1.

DETAILED DESCRIPTION

Described herein is a process for oligomerizing isobutene in a feedstock wherein the feedstock is contacted with a catalyst comprising a MCM-22 family molecular sieve under conditions, including a temperature from about 45° C. to less than 140° C., effective to oligomerize the isobutene and produce an effluent containing less isobutene than in the feedstock.

The feedstock can be any process stream containing isobutene, including a pure isobutene stream. In general, however, the feedstock is an olefinic $C_4$ hydrocarbon mixture containing isobutene and at least one linear butene, namely butene-1, cis-butene-2, trans-butene-2 or mixtures thereof. Such olefinic $C_4$ hydrocarbon mixtures can be obtained by steam cracking of ethane, propane, butane, LPG and light naphthas; catalytic cracking of naphthas and other refinery feedstocks; and by conversion of oxygenates, such as methanol, to lower olefins. The present oligomerization process then serves to reduce the isobutene concentration of the olefinic $C_4$ hydrocarbon mixture.

For example, the following olefinic $C_4$ hydrocarbon mixtures are generally available in any refinery employing steam cracking to produce olefins: a crude steam cracked butene stream, Raffinate-1 (the product remaining after solvent extraction or hydrogenation to remove butadiene from a crude steam cracked butene stream) and Raffinate-2 (the product remaining after removal of butadiene and isobutene from a crude steam cracked butene stream). Generally, these streams have compositions within the weight ranges indicated in Table 1 below.

TABLE 1

| Component | Crude $C_4$ stream | Raffinate 1 | | Raffinate 2 | |
|---|---|---|---|---|---|
| | | Solvent Extraction | Hydrogenation | Solvent Extraction | Hydrogenation |
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed $C_4$ streams, such as those obtained by catalytic cracking of naphthas and other refinery feedstocks, typically have the following composition:

Propylene=0-2 wt %
Propane=0-2 wt %
Butadiene=0-5 wt %
Butene-1=5-20 wt %
Butene-2=10-50 wt %
Isobutene=5-25 wt %
Iso-butane=10-45 wt %
N-butane=5-25 wt %

$C_4$ hydrocarbon fractions obtained from the conversion of oxygenates, such as methanol, to lower olefins more typically have the following composition:

Propylene=0-1 wt %
Propane=0-0.5 wt %
Butadiene=0-1 wt %
Butene-1=10-40 wt %
Butene-2=50-85 wt %
Isobutene=0-10 wt %
N-+iso-butane=0-10 wt %

Any one or any mixture of the above $C_4$ hydrocarbon mixtures can be used in the present isobutene oligomerization process.

In addition to other hydrocarbon components, commercial $C_4$ hydrocarbon mixtures typically contain other impurities which could be detrimental to the present oligomerization process or to use of the hydrocarbon mixture downstream of the present oligomerization process. For example, refinery $C_4$ hydrocarbon streams typically contain nitrogen and sulfur impurities, whereas $C_4$ hydrocarbon streams obtained by oxygenate conversion processes typically contain unreacted oxygenates and water. Thus, prior to the present oligomerization step, these mixtures may also be subjected to one or more of sulfur removal, nitrogen removal and oxygenate removal. Removal of sulfur and/or nitrogen and/or oxygenate impurities is conveniently effected by one or a combination of any of caustic treatment, water washing, distillation, adsorption using molecular sieves and membrane separation. Water is also typically removed by adsorption.

Conveniently, the feed to the present oligomerization process contains, by weight, less than 1000 ppm, such as less than 500 ppm, for example less than 100 ppm, water. Typically, the feed contains less than 100 ppm, such as less than 30 ppm, for example less than 3 ppm, sulfur. Conveniently, the feed contains less than 10 ppm, such as less than 1 ppm, for example less than 0.1 ppm, nitrogen. Ideally, the feed contains less than 1000 ppm water and less than 100 ppm sulfur and less than 10 ppm nitrogen, such as less than 500 ppm, 30 ppm, 1 ppm water, sulfur, nitrogen respectively, most preferably less than 100 ppm, 3 ppm, 0.1 ppm water, sulfur, nitrogen respectively.

The oligomerization catalyst employed in the present process is at least one molecular sieve of the MCM-22 family. As used herein, the term "MCM-22 family material" (or "material of the MCM-22 family" or "molecular sieve of the MCM-22 family" or "MCM-22 family zeolite"), includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Generally, the molecular sieve is selected from (a) MCM-49, (b) MCM-56 and (c) isotypes of MCM-49 and MCM-56, such as ITQ-2.

The MCM-22 family molecular sieve can be used in the present process in unbound (neat) form, or can be combined with a conventional metal oxide binder, such as alumina.

The present oligomerization process is conducted at a relatively low temperature of from about 45° C. to less than 140° C., such as from about 50° C. to about 120° C. The pressure employed in the process is not closely controlled, but generally will be between about 345 and about 13790 kPag (about 50 and about 2000 psig), typically between about 1379 and about 5516 kPag (about 200 and about 800 psig), such that at least the butenes are substantially in the liquid phase during the oligomerization process. The process can be conducted as a continuous or a batch process, and in the case of the more preferred continuous process, the butene feed is preferably contacted with the catalyst at a LHSV of about 4 to about 16. In addition, the process can be conducted in any suitable reaction zone such as, for example, in a flow reactor containing a fixed catalyst bed or in a catalytic distillation reactor. Staged reaction in a number of series-connected reaction zones is also contemplated.

The present process selectively converts isobutene in an olefinic $C_4$ hydrocarbon mixture to heavier products, mainly branched $C_8$ and $C_{12}$ oligomers, which can readily be separated from the product effluent by distillation. Of course, in the case of catalytic distillation, reaction and separation may occur simultaneously. After separation, the oligomers, eg the $C_8$ and $C_{12}$ oligomers can be hydrogenated and used for fuel or other applications, including solvents. The remaining isobutene deficient $C_4$ hydrocarbon mixture can then be used as a feed, for example, in the production of sec-butylbenzene.

Although the MCM-22 family zeolites employed in the present oligomerization process are highly resistant to the aging problems reported with other zeolitic materials, such as zeolite beta, in practice the catalyst will tend to slowly lose activity and require rejuvenation and/or regeneration. The catalyst may be rejuvenated by treatment in an inert liquid (such as a non-olefinic hydrocarbon), and may be regenerated by contacting at elevated temperature with an oxygen-containing gas.

The oligomerization process described herein employing MCM-22 family molecular sieves as a catalyst is effective in selectively removing isobutene from hydrocarbon feedstocks comprising isobutene and at least one additional $C_4$ alkene. In particular, the process is effective in reducing the isobutene content of a stream containing up to 5 wt % isobutene, such as Raffinate-2, to less than 0.3 wt %, such as to less than 0.2 wt %, even to less than 0.15 wt %. Moreover, even with a feedstock containing at least 90 wt % of n-butenes, the present process oligomerizes no more than 12 wt % of said n-butenes. The resultant isobutene-deficient effluent can then be used as a feedstock for, for example, a linear butene oligomerization process to produce higher ($C_8$+) olefins or for the alkylation of benzene with linear butenes to produce sec-butylbenzene.

The alkylation of benzene with linear butenes using a MCM-22 family molecular sieve as the catalyst is described in International Patent Publication No. WO06/015826, the entire contents of which are incorporated herein by reference. In particular, it is found that, by using the present oligomerization process to reduce the isobutene content of a butene-containing feedstock, such as Raffinate-2, to less than 0.2 wt %, the resultant feed can be used to alkylate benzene with a high selectivity to sec-butylbenzene. Moreover, the amounts of tert-butylbenzene and butene oligomers produced during the alkylation step are reduced to very low levels. The resultant sec-butylbenzene product can then be converted to phenol and methyl ethyl ketone by oxidizing the sec-butylbenzene to produce sec-butylbenzene hydroperoxide and then cleaving the hydroperoxide. It is an advantage of the invention that the catalyst employed for the selective oligomerization of the isobutene can also be employed, under alkylation conditions, to alkylate benzene using the effluent from the oligomerization reaction.

The invention will now be more particularly described with reference to the Examples.

Example 1

Selective Isobutene Dimerization with MCM-22 Catalyst

A fresh MCM-22 catalyst with a nominal weight composition of 65% MCM-22 crystal and 35% Versal 300 alumina was used for the experiment. The catalyst was made by extruding the MCM-22 crystal with Versal 300 alumina into 1.6 mm (1/16 inch) diameter cylindrical extrudate. The extrudate was cut to 1.3 mm (1/20 inch) length and 0.25 g (0.5 cc) of this sized catalyst was used. The catalyst was diluted with sand to 3 cc and loaded into an isothermal, down-flow, fixed-bed, tubular reactor having an outside diameter of 4.76 mm (3/16 inch). The catalyst was dried at 260° C. and 1 atm for 2 hours with 100 cc/min flowing nitrogen. Nitrogen was turned off and the reactor was cooled to 69° C. Mixed butenes (see Table 1 for feed composition) was introduced into the reactor at 60 cc/hr until reactor pressure reached 3448 kPag (500 psig). Butene flow was then reduced to 6.0 cc/hr (12 LHSV). The product composition was analyzed online every 4 hours by an HP GC equipped with two parallel columns, a 60M BD-1 column and a 50M PLOT column. Liquid samples were collected daily to ensure material closure. Data were collected at 3448 kPag (500 psig) with temperature set at 69, 76, 83, and 90° C. respectively. Representative data are shown in Table 2.

TABLE 2

| Sample ID | Feed | | | | |
|---|---|---|---|---|---|
| Days on Stream | | 16.7 | 18.5 | 19.7 | 23.0 |
| Temperature, ° C. | | 69 | 76 | 83 | 90 |
| Composition, wt % | | | | | |
| Isobutane | 0.002 | 0.012 | 0.012 | 0.013 | 0.012 |
| n-Butane | 0.094 | 0.096 | 0.096 | 0.096 | 0.096 |
| t-Butene | 41.285 | 40.610 | 40.527 | 40.575 | 40.522 |
| 1-Butene | 0.092 | 0.098 | 0.104 | 0.164 | 0.223 |
| Isobutene | 4.538 | 0.316 | 0.184 | 0.119 | 0.081 |
| c-Butene | 53.428 | 48.942 | 48.708 | 48.396 | 47.886 |
| Butadiene | 0.477 | 0.433 | 0.409 | 0.381 | 0.343 |
| $C_5$-$C_7$ | 0.083 | 0.195 | 0.199 | 0.199 | 0.201 |
| $C_8^=$ | 0.000 | 7.621 | 8.200 | 8.515 | 9.018 |
| $C_9^+$ | 0.000 | 1.675 | 1.559 | 1.540 | 1.615 |
| Sum | 100.0 | 100.0 | 100.0 | 100.0 | 100.0 |

TABLE 2-continued

| Sample ID | Feed | | | | |
|---|---|---|---|---|---|
| Conversion % | | | | | |
| Isobutene | | 93.0 | 95.9 | 97.4 | 98.2 |
| Butadiene | | 9.2 | 14.3 | 20.1 | 28.1 |
| n-Butenes | | 5.4 | 5.8 | 6.0 | 6.5 |
| Selectivity, wt % | | | | | |
| $C_5$-$C_7$ | | 1.18 | 1.17 | 1.14 | 1.09 |
| $C_8^=$ | | 81.01 | 83.04 | 83.72 | 83.88 |
| $C_9^+$ | | 17.81 | 15.79 | 15.14 | 15.02 |
| Sum | | 100.0 | 100.0 | 100.0 | 100.0 |

The flow was then reduced to 3.6 cc/hr (7.2 LHSV) and more data were collected at 3448 kPag (500 psig) with temperature set at 90, 83, 76, and 69 respectively. Representative data are shown in Table 3.

TABLE 3

| Sample ID | Feed | | | | |
|---|---|---|---|---|---|
| Days on Stream | | 27.9 | 26.9 | 26.0 | 25.0 |
| Temperature, ° C. | | 69 | 76 | 83 | 90 |
| Composition, wt % | | | | | |
| Isobutane | 0.002 | 0.012 | 0.015 | 0.014 | 0.012 |
| n-Butane | 0.094 | 0.096 | 0.099 | 0.095 | 0.096 |
| t-Butene | 41.285 | 40.570 | 40.516 | 40.461 | 40.305 |
| 1-Butene | 0.092 | 0.105 | 0.144 | 0.214 | 0.325 |
| Isobutene | 4.538 | 0.139 | 0.076 | 0.042 | 0.021 |
| c-Butene | 53.428 | 48.935 | 48.521 | 47.867 | 46.849 |
| Butadiene | 0.477 | 0.425 | 0.396 | 0.344 | 0.283 |
| $C_5$-$C_7$ | 0.083 | 0.181 | 0.192 | 0.191 | 0.201 |
| $C_8^=$ | 0.000 | 7.935 | 8.391 | 9.003 | 9.758 |
| $C_9^+$ | 0.000 | 1.600 | 1.649 | 1.765 | 2.149 |
| Sum | 100.0 | 100.0 | 100.0 | 100.0 | 100.0 |
| Conversion % | | | | | |
| Isobutene | | 96.93 | 98.34 | 99.07 | 99.54 |
| Butadiene | | 10.83 | 16.93 | 27.83 | 40.58 |
| n-Butenes | | 5.48 | 5.93 | 6.61 | 7.73 |
| Selectivity, wt % | | | | | |
| $C_5$-$C_7$ | | 1.01 | 1.07 | 0.99 | 0.98 |
| $C_8^=$ | | 82.37 | 82.68 | 82.78 | 81.15 |
| $C_9^+$ | | 16.61 | 16.25 | 16.23 | 17.87 |
| Sum | | 100.00 | 100.00 | 100.00 | 100.00 |

The data in Tables 1 and 2 show that MCM-22 is active and selective for converting isobutene to dimers or $C_8^=$. The temperature required for the reaction was mild, in the range of 69-90° C. Very low levels of isobutene can be obtained by adjusting reaction temperature and/or flow rate.

The data are further shown in FIGS. 1 and 2. FIG. 1 shows the effect of reaction temperature and feed flow rate on isobutene level. For example, to achieve an isobutene level of 0.07-0.08 wt % in the reactor effluent, the reactor could be operated at 76° C. and 7.2 LHSV or at 90° C. and 12 LHSV. To achieve an isobutene level of 0.12-0.14 wt % in the reactor effluent, the reactor could be operated at 69° C. and 7.2 LHSV or at 83° C. and 12 LHSV. FIG. 2 shows the n-butene conversion as a function of isobutene level in the reactor effluent. For each mole of isobutene converted, about 1 mole of n-butene was also converted. n-Butene conversion increased to a higher level as expected when the target isobutene level is very low.

Example 2

Sec-Butylbenzene Production Using MCM-22 Catalyst and 2-Butene Feed

A 1.0 gram sample of the same MCM-22 catalyst (65% MCM-22/35% alumina binder) as used in Example 1 was used for the alkylation of benzene with 2-butene. The catalyst was in the form of a 1.6 mm (1/16 inch) diameter cylindrical extrudate, chopped to 1.6 mm (1/16 inch) length, and was diluted with sand to 3 cc and loaded into an isothermal, down-flow, fixed-bed, tubular reactor having an outside diameter of 4.76 mm (3/16 inch). The catalyst was dried at 150° C. and 1 atm with 100 cc/min flowing nitrogen for 2 hours. The nitrogen was turned off and benzene was fed to the reactor at 60 cc/hr until reactor pressure reached the desired 2068 kPag (300 psig). Benzene flow was then reduced to 7.63 cc/hr (6.67 WHSV). Butene feed (99.28% 2-butene, 0.39% n-butane, 0.15% isobutene, and 0.18% others) was introduced from a syringe pump at 2.57 cc/hr (1.6 WHSV). Feed benzene/butene molar ratio was maintained at 3:1 for the entire run. The reactor temperature was adjusted to 160° C. Liquid products were collected at reactor conditions of 160° C. and 2068 kPag (300 psig) in a cold-trap and analyzed off line. 2-Butene conversion was determined by measuring unreacted 2-butene relative to feed 2-butene. The catalyst was on stream for 4 days at 1.6 WHSV of butene with 97% 2-butene conversion, 2 days at 4.8 WHSV with 95% conversion, then 1 day at 7.2 WHSV with 86% conversion, and followed by 4 days again at 1.6 WHSV with 97% conversion. No deactivation was detected during the 11-day test cycle. Representative data are shown in Table 4. Relative activity of MCM-22 based on first-order butene conversion was 1.0.

TABLE 4

| Days on Stream | 3.8 | 5.9 | 7.1 | 10.8 |
|---|---|---|---|---|
| Butene WHSV, h$^{-1}$ | 1.6 | 4.8 | 7.2 | 1.6 |
| 2-Butene Conv, % | 97.7 | 95.3 | 86.0 | 97.2 |
| Product Selectivity, wt % | | | | |
| Iso-Butane | 0.010 | 0.001 | 0.004 | 0.008 |
| Iso-Butene & 1-Butene | 0.000 | 0.020 | 0.355 | 0.000 |
| $C_5$-$C_7$ | 0.227 | 0.105 | 0.132 | 0.120 |
| $C_8$ and $C_{12}$ (butene oligomers) | 0.812 | 1.753 | 2.556 | 1.910 |
| Cumene | 0.077 | 0.050 | 0.031 | 0.059 |
| t-Butylbenzene | 0.158 | 0.060 | 0.026 | 0.103 |
| iso-Butylbenzene* | 0.000 | 0.000 | 0.000 | 0.000 |
| sec-Butylbenzene | 89.185 | 90.983 | 90.490 | 91.553 |
| n-Butylbenzene | 0.024 | 0.031 | 0.030 | 0.025 |
| Di-butylbenzene | 8.012 | 6.589 | 5.982 | 5.791 |
| Tri-butylbenzene | 1.239 | 0.420 | 0.392 | 0.417 |
| Heavies | 0.256 | 0.008 | 0.003 | 0.013 |
| Sum | 100.0 | 100.0 | 100.0 | 100.0 |
| Butylbenzene Composition, % | | | | |
| t-Butylbenzene | 0.177 | 0.065 | 0.029 | 0.112 |
| iso-Butylbenzene* | 0.000 | 0.000 | 0.000 | 0.000 |
| sec-Butylbenzene | 99.796 | 99.900 | 99.938 | 99.860 |
| n-Butylbenzene | 0.027 | 0.034 | 0.033 | 0.028 |
| Sum | 100.0 | 100.0 | 100.0 | 100.0 |

*iso-Butylbenzene less than 0.5% in total butylbenzene not detectable with GC used.

The results in Table 4 show that, with a 2-butene feed containing only 0.15% isobutene, MCM-22 is effective in alkylating benzene at 95%+2-butene conversion with a selectivity to sec-butylbenzene in excess of 90%.

Example 3

Sec-Butylbenzene Production Using MCM-49 Catalysts and 2-Butene Feed

The process of Example 2 was repeated but with the MCM-22 catalyst replaced by 0.6 gm of MCM-49. The 1.3 mm (1/20 inch) quadrulobe extrudate with 60% MCM-49/40% Versal 200 alumina binder was cut to 1.3 mm (1/20 inch) length. The catalyst was on stream for 4 days at 2.7 WHSV of butene with 97-98% butene conversion, 1 day at 8 WHSV with 97% conversion, 0.5 days at 12 WHSV with 93% conversion, 1.6 days at 2.7 WHSV with 98% conversion, 0.3 days at 19.2 WHSV with 86% conversion, and followed by 0.7 days at 2.7 WHSV again with 98% conversion. Relative activity of MCM-49 based on first-order butene conversion was 2.4. Representative data are shown in Table 5.

TABLE 5

| Days on Stream | 1.0 | 3.9 | 4.7 | 6.9 | 7.1 | 7.9 |
|---|---|---|---|---|---|---|
| Butene WHSV, h$^{-1}$ | 2.7 | 2.7 | 8.0 | 2.7 | 19.2 | 2.7 |
| 2-Butene Conv, % | 97.6 | 97.3 | 96.7 | 97.7 | 86.3 | 97.6 |
| Product Selectivity, wt % | | | | | | |
| Iso-Butane | 0.006 | 0.007 | 0.004 | 0.005 | 0.003 | 0.003 |
| Iso-Butene & 1-Butene | 0.000 | 0.000 | 0.000 | 0.000 | 0.358 | 0.000 |
| $C_5$-$C_7$ | 0.164 | 0.109 | 0.109 | 0.107 | 0.089 | 0.111 |
| $C_8$ and $C_{12}$ (butene oligomers) | 0.586 | 1.144 | 1.428 | 1.418 | 1.852 | 1.308 |
| Cumene | 0.054 | 0.057 | 0.045 | 0.060 | 0.042 | 0.043 |
| t-Butylbenzene | 0.125 | 0.128 | 0.069 | 0.105 | 0.042 | 0.091 |
| iso-Butylbenzene* | 0.000 | 0.000 | 0.000 | 0.000 | 0.000 | 0.000 |
| sec-Butylbenzene | 92.659 | 92.319 | 92.400 | 92.693 | 91.759 | 93.513 |
| n-Butylbenzene | 0.012 | 0.023 | 0.025 | 0.028 | 0.013 | 0.013 |
| Di-butylbenzene | 5.818 | 5.752 | 5.664 | 5.266 | 5.649 | 4.672 |
| Tri-butylbenzene | 0.513 | 0.425 | 0.250 | 0.304 | 0.189 | 0.241 |
| Heavies | 0.062 | 0.036 | 0.006 | 0.016 | 0.006 | 0.007 |
| Sum | 100.0 | 100.0 | 100.0 | 100.0 | 100.0 | 100.0 |
| Butylbenzene Comp. % | | | | | | |
| t-Butylbenzene | 0.135 | 0.139 | 0.075 | 0.113 | 0.046 | 0.097 |
| iso-Butylbenzene* | 0.000 | 0.000 | 0.000 | 0.000 | 0.000 | 0.000 |

TABLE 5-continued

| Days on Stream | 1.0 | 3.9 | 4.7 | 6.9 | 7.1 | 7.9 |
|---|---|---|---|---|---|---|
| sec-Butylbenzene | 99.852 | 99.836 | 99.898 | 99.857 | 99.940 | 99.889 |
| n-Butylbenzene | 0.013 | 0.025 | 0.027 | 0.030 | 0.014 | 0.014 |
| Sum | 100.0 | 100.0 | 100.0 | 100.0 | 100.0 | 100.0 |

*iso-Butylbenzene less than 0.5% in total butylbenzene not detectable with GC used.

The results in Table 5 show that, with a 2-butene feed containing only 0.15% isobutene, MCM-49 is effective in alkylating benzene at 95%+2-butene conversion with a selectivity to sec-butylbenzene in excess of 92%.

Example 4

Sec-Butylbenzene Production with MCM-22 Catalyst and Raffinate-2 Type Feed

A 1.0 gram sample of the MCM-22 catalyst (65 wt % MCM-22/35% alumina binder) from Example 1 was used for the alkylation of benzene with Raffinate-2 type feed. The Raffinate-2 type feed was a synthetic blend with the following weight composition: 53.43% cis-butene, 41.29% trans-butene, 4.54% isobutene, 0.48% butadiene, 0.09% 1-butene, 0.09% n-butane, and 0.1% others. The catalyst was in the form of a 1.6 mm (1/16 inch) diameter cylindrical extrudate and was diluted with sand to 3 cc and loaded into an isothermal, down-flow, fixed-bed, tubular reactor having an outside diameter of 4.76 mm (3/16 inch). The catalyst was dried at 150° C. and 1 atm with 100 cc/min flowing nitrogen for 2 hours. The nitrogen was turned off and benzene was fed to the reactor at 60 cc/hr until reactor pressure reached the desired 2068 kPag (300 psig). Benzene flow was then reduced to 7.63 cc/hr (6.67 WHSV) and Raffinate-2 type feed was introduced from a syringe pump at 2.57 cc/hr (1.6 WHSV). The reactor temperature was adjusted to 160° C. Feed benzene/butene molar ratio was maintained at 3:1 for the entire run. Liquid product was collected in a cold-trap and analyzed off line. Butene conversion was determined by measuring unreacted butene relative to feed butene. The catalyst was on stream for 6 days at 1.6 WHSV of butene with 98% 2-butene conversion, 1 day at 4.8 WHSV with 80% conversion, 1 day at 7.2 WHSV with 62% conversion, and followed by 4 days again at 1.6 WHSV with 97% conversion. Representative data are shown in Table 6. Relative activity of MCM-22 based on first-order butene conversion was 0.5.

TABLE 6

| Sample # | 1 | 3 | 6 | 8 | 11 | 13 | 15 |
|---|---|---|---|---|---|---|---|
| Days on Stream | 0.79 | 2.79 | 5.79 | 7.33 | 8.19 | 9.8 | 11.79 |
| Butene WHSV, h$^{-1}$ | 1.6 | 1.6 | 1.6 | 4.8 | 7.2 | 1.6 | 1.6 |
| 2-Butene Conv, % | 98.6 | 98.0 | 98.4 | 79.8 | 62.1 | 96.9 | 97.0 |
| Isobutene Conv, % | 98.2 | 96.3 | 96.8 | 64.4 | 35.8 | 93.7 | 94.0 |
| Butadiene Conv, % | 100.0 | 100.0 | 100.0 | 100.0 | 96.4 | 100.0 | 100.0 |
| Product Selectivity, wt % | | | | | | | |
| i-C$_4$ | 0.047 | 0.039 | 0.034 | 0.023 | 0.025 | 0.027 | 0.025 |
| C$_5$-C$_7$ | 0.388 | 0.525 | 0.467 | 0.541 | 0.640 | 0.556 | 0.555 |
| C$_8$ and C$_{12}$ (butene oligomers) | 8.739 | 7.886 | 7.746 | 10.343 | 12.852 | 7.916 | 8.230 |
| Cumene | 0.175 | 0.183 | 0.189 | 0.183 | 0.194 | 0.196 | 0.172 |
| t-Butylbenzene | 2.319 | 1.577 | 1.521 | 0.697 | 0.561 | 1.267 | 1.224 |
| iso-Butylbenzene* | 0.000 | 0.000 | 0.000 | 0.000 | 0.000 | 0.000 | 0.000 |
| sec-Butylbenzene | 81.330 | 83.058 | 83.282 | 82.789 | 81.265 | 83.453 | 83.406 |
| n-Butylbenzene | 0.034 | 0.059 | 0.055 | 0.063 | 0.058 | 0.060 | 0.062 |
| Di-butylbenzene | 5.227 | 5.559 | 5.580 | 4.642 | 3.972 | 5.465 | 5.312 |
| Tri-butylbenzene | 1.456 | 0.887 | 0.926 | 0.495 | 0.378 | 0.837 | 0.840 |
| Heavies | 0.284 | 0.225 | 0.200 | 0.225 | 0.055 | 0.224 | 0.174 |
| Sum | 100.0 | 100.0 | 100.0 | 100.0 | 100.0 | 100.0 | 100.0 |
| Butylbenzene Composition, % | | | | | | | |
| t-Butylbenzene | 2.772 | 1.863 | 1.792 | 0.835 | 0.685 | 1.494 | 1.445 |
| iso-Butylbenzene* | 0.000 | 0.000 | 0.000 | 0.000 | 0.000 | 0.000 | 0.000 |
| sec-Butylbenzene | 97.187 | 97.817 | 98.143 | 99.091 | 99.244 | 98.435 | 98.482 |
| n-Butylbenzene | 0.041 | 0.070 | 0.064 | 0.075 | 0.071 | 0.071 | 0.073 |
| Sum | 100.0 | 100.0 | 100.0 | 100.0 | 100.0 | 100.0 | 100.0 |

*iso-Butylbenzene less than 0.5% in total butylbenzene not detectable with GC used.

Table 6 shows that the MCM-22 catalyst was effective for sec-butylbenzene production using a Raffinate-2 type feed. The 0.5% butadiene in butene feed had no significant effect on MCM-22 stability during the 12-day test cycle. However, the 4.5% isobutene in the butene feed increased by-product formation. After initial lineout, selectivity measured at 97-98% 2-butene conversion was 8% for butene oligomers, 1.2-1.5% for t-butylbenzene, and 83% for sec-butylbenzene. This was a significant change when compared to results in Table 4 using the same catalyst and 2-butene feed. Selectivity measured with 2-butene feed at 97-98% 2-butene conversion was 1-2% for butene oligomers, 0.1-0.2% for t-butylbenzene, and 89-91% for sec-butylbenzene. The use of Raffinate-2 type feed resulted a 50% activity drop for MCM-22.

Example 5

Sec-Butylbenzene Production with MCM-49 Catalyst and Raffinate-2 Type Feed

The process of Example 4 was repeated but with the MCM-22 catalyst replaced by 0.5 gm of MCM-49. This is the same catalyst used in Example 2. The 1.3 mm (1/20 inch) quadrulobe extrudate with 60% MCM-49/40% Versal 200 alumina binder was cut to 1.3 mm (1/20 inch) length. The MCM-49 was on stream for 3 days at 3.2 WHSV of butene with 96% conversion, 1 day at 9.6 WHSV with 80-83% conversion, and 3 days at 3.2 WHSV with 95% conversion. Representative data are shown in Table 7. Relative activity of MCM-49 based on first-order butene conversion was 1.1.

TABLE 7

| Sample # | 2 | 5 | 8 |
|---|---|---|---|
| Days on Stream | 2.3 | 3.2 | 5.3 |
| Butene WHSV, h$^{-1}$ | 3.2 | 9.6 | 3.2 |
| 2-Butene Conv, % | 96.1 | 83.0 | 95.5 |
| Isobutene Conv, % | 97.7 | 67.2 | 92.8 |
| Butadiene Conv, % | 100.0 | 100.0 | 100.0 |
| Product Selectivity, wt % | | | |
| i-C$_4$ | 0.041 | 0.032 | 0.028 |
| C$_5$-C$_7$ | 0.527 | 0.503 | 0.583 |
| C$_8$ and C$_{12}$ (butene oligomers) | 7.688 | 9.732 | 8.185 |
| Cumene | 0.128 | 0.144 | 0.127 |
| t-Butylbenzene | 1.849 | 0.849 | 1.240 |
| iso-Butylbenzene* | 0.000 | 0.008 | 0.012 |
| sec-Butylbenzene | 82.977 | 84.284 | 84.720 |
| n-Butylbenzene | 0.062 | 0.059 | 0.068 |
| Di-butylbenzene | 5.431 | 3.878 | 4.273 |
| Tri-butylbenzene | 1.079 | 0.429 | 0.629 |
| Heavies | 0.218 | 0.082 | 0.134 |
| Sum | 100.0 | 100.0 | 100.0 |
| Butylbenzene Composition, % | | | |
| t-Butylbenzene | 2.179 | 0.996 | 1.441 |
| iso-Butylbenzene* | 0.000 | 0.010 | 0.013 |
| sec-Butylbenzene | 97.749 | 98.925 | 98.467 |
| n-Butylbenzene | 0.073 | 0.069 | 0.078 |
| Sum | 100.0 | 100.0 | 100.0 |

*iso-Butylbenzene less than 0.5% in total butylbenzene not detectable with GC used.

Table 7 shows that MCM-49 catalyst was also effective for sec-butylbenzene production using a Raffinate-2 type feed. The 0.5% butadiene in butene feed had no significant effect on MCM-49 stability during the 7-day test cycle. Again, however, the 4.5% isobutene in the butene feed increased by-product formation. Selectivity measured at 96% 2-butene conversion was 8% for butene oligomers, 1.2-1.8% for t-butylbenzene, and 83-85% for sec-butylbenzene. This is a significant change when compared to results in Table 5 using the same MCM-49 catalyst and 2-butene feed. Selectivity measured with 2-butene feed at 97% 2-butene conversion was 1.5% or less for butene oligomers, 0.1% for t-butylbenzene, and 92% for sec-butylbenzene. The use of Raffinate-2 type feed resulted a 50% activity drop for MCM-49.

The above examples show that reducing the level of isobutene to below 0.2% in the mixed butene feed to alkylation gives reduced level of t-butylbenzene and reduced selectivity (less than 4%, typically less than 2.5%) to C$_8$-C$_{12}$ oligomers in the alkylation product.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for oligomerizing isobutene, the process comprising contacting a feedstock comprising 2 wt. % to 5 wt. % isobutene with a catalyst comprising a MCM-22 family molecular sieve under conditions effective to oligomerize said isobutene, said conditions including a temperature from 45° C. to less than 140° C., to produce a first effluent comprising isobutene oligomers and less than 0.3 wt. % isobutene; wherein the feedstock comprises at least 90 wt % of n-butenes and the contacting step oligomerizes no more than 12 wt % of the n-butenes.

2. The process of claim 1 wherein said conditions include a temperature from 50° C. to 120° C.

3. The process of claim 1 wherein said conditions include a pressure of from 345 to 13790 kPag (50 to 2000 psig).

4. The process of claim 3 wherein the pressure is from 1379 to 5516 kPag (200 to 800 psig).

5. The process of claim 1, wherein the molecular sieve has an X-ray diffraction pattern including d-spacing maxima at 12.4±0.25, 6.9±0.15, 3.57±0.07 and 3.42±0.07 Angstrom.

6. The process of claim 1, wherein the molecular sieve is selected from MCM-22, PSH-3, SSZ-25, ERB-1, ITQ-1, ITQ-2, MCM-36, MCM-49, MCM-56, UZM-8, and combinations of any two or more thereof.

7. The process of claim 6 wherein the molecular sieve is selected from MCM-22, MCM-49, MCM-56 and combinations of any two or more thereof.

8. The process of claim 1 and further comprising separating the isobutene oligomers from the first effluent to produce a second effluent rich in butene-1 and/or butene-2 and using the second effluent as a feedstock for oligomerization to produce higher olefins with low branching.

9. The process of claim 1 and further comprising using the first effluent as a feedstock for the alkylation of benzene in the presence of an alkylation catalyst to produce sec-butylbenzene.

10. The process of claim 1 and further comprising separating the isobutene oligomers from the first effluent to produce a second effluent rich in butene-1 and/or butene-2 and using the second effluent as a feedstock for the alkylation of benzene in the presence of an alkylation catalyst to produce sec-butylbenzene.

11. A process for producing sec-butylbenzene, the process comprising:
   (a) contacting a C$_4$ hydrocarbon feedstock comprising 2 wt. % to 5 wt. % isobutene and at least one n-butene with a catalyst comprising a MCM-22 family molecular sieve under conditions effective to selectively oligomerize the isobutene, said conditions including a temperature from 45° C. to less than 140° C. and said contacting producing a first effluent comprising isobutene oligomers, said at least one n-butene, and less than 0.3 wt. % isobutene;
   (b) separating the isobutene oligomers from the first effluent to produce a second effluent rich in said at least one n-butene;
   (c) contacting the second effluent with benzene under alkylation conditions and in the presence of an alkylation catalyst to produce sec-butylbenzene wherein the C4 hydrocarbon feedstock comprises at least 90 wt % of n-butenes and the contacting (a) oligomerizes no more than 12 wt % of the n-butenes.

12. The process of claim 11 wherein the first effluent contains less than 0.2 wt % isobutene.

13. The process of claim 11 wherein the conditions in contacting (a) include a temperature from 50° C. to 120° C.

14. The process of claim 11 wherein the conditions in contacting (a) include a pressure of from 345 to 13790 kPag (50 to 2000 psig).

15. The process of claim 11 and further comprising:
(d) contacting the first effluent with water and/or an alcohol prior to said separating (b), said contacting (d) converting at least part of any isobutene remaining in said effluent to an ether.

16. The process of claim 11 wherein the alkylation catalyst comprises a MCM-22 family molecular sieve.

17. The process of claim 11 and further comprising:
(e) oxidizing the sec-butylbenzene from (c) to produce a hydroperoxide; and
(f) cleaving the hydroperoxide from (e) to produce phenol and methyl ethyl ketone.

\* \* \* \* \*